(12) United States Patent
Taylor

(10) Patent No.: US 8,426,666 B2
(45) Date of Patent: *Apr. 23, 2013

(54) ISOMERIZATION OF WET HEXANES

(75) Inventor: Bradley M. Taylor, Tulsa, OK (US)

(73) Assignee: Phillips 66 Company, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/633,458

(22) Filed: Dec. 8, 2009

(65) Prior Publication Data

US 2010/0210888 A1  Aug. 19, 2010

Related U.S. Application Data

(63) Continuation-in-part of application No. 12/371,997, filed on Feb. 17, 2009, now Pat. No. 7,659,438.

(51) Int. Cl.
*C07C 5/27* (2006.01)

(52) U.S. Cl.
USPC ........................................... 585/750; 585/751

(58) Field of Classification Search .................. 585/750, 585/751

See application file for complete search history.

(56) References Cited

U.S. PATENT DOCUMENTS

| | | | |
|---|---|---|---|
| 2,841,626 A * | 7/1958 | Holzman et al. | 585/748 |
| 5,837,641 A | 11/1998 | Gosling et al. | |
| 6,080,904 A | 6/2000 | Chang et al. | |
| 6,140,547 A | 10/2000 | Lin et al. | |
| 6,767,859 B2 | 7/2004 | Ying et al. | |
| 6,977,322 B2 | 12/2005 | Gillespie | |
| 7,304,199 B2 | 12/2007 | Xu et al. | |

OTHER PUBLICATIONS

A. Corma et al, "Discovery of new paraffin isomerization catalysts based on SO42-/ZrO2 and WOx/ZrO2 applying combinatorial techniques", Catalysis Today, vol. 81, Issue 3, Jun. 30, 2003, pp. 495-506.

Jose M. Serra et al, "Development of a low temperature light paraffin isomerization catalysts with improved resistance to water and sulphur by combinatorial methods", applied Catalysis A: General, vol. 239, Issues 1-2, Jan. 30, 2003, pp. 35-42.

T. N. Vu et al, "Platinum-tungstated zirconia isomerization catalysts: Part II, Effect of platinum and tungsten loading on the mechanism of isomerization of n-hexane: a kinetic study", Journal of Catalysis, vol. 231, Issue 2, Apr. 25, 2005, pp. 468-479.

Wenling Chu et al, "Gas-phase hydration of ethene over tungstena-zirconia", applied catalysis A: General, vol. 259, Issue 2, Mar. 15, 2004, pp. 199-205.

Material Safety Data Sheet (MSDS), No. 8035-09, Zeolyst International, Jan. 25, 2005.

Z-700A Paraffin Isomerization Catalyst, Zeolyst International, http://www.zeolyst.com/html/Z700A.asp, printed Feb. 12, 2009.

* cited by examiner

*Primary Examiner* — Thuan D Dang
(74) *Attorney, Agent, or Firm* — Phillips 66 Company

(57) ABSTRACT

A method to isomerize one or more wet hexanes in the presence of a catalyst comprising tungsten, zirconium and a Group VIII metal is provided.

9 Claims, No Drawings

ISOMERIZATION OF WET HEXANES

CROSS-REFERENCE TO RELATED APPLICATIONS

This application is a continuation-in-part of U.S. patent application Ser. No. 12/371,997, filed Feb. 17, 2009, now U.S. Pat. No. 7,659,438 which is herein incorporated by reference.

STATEMENT REGARDING FEDERALLY SPONSORED RESEARCH OR DEVELOPMENT

None.

BACKGROUND OF THE INVENTION

1. Field of the Invention

The present invention relates generally to isomerization of wet hexanes.

2. Description of the Prior Art

Current catalytic materials used for isomerization of hexanes, such as n-hexane, wet hexanes, and other hexanes, are not very tolerant to water, oxygenates and sulfur compounds. The most active industrially employed catalytic materials, such as, for example, platinum on chlorided-alumina, require extensive hexanes, i.e., feed, pretreatment to completely remove water, sulfur, and oxygenates. Modern zeolite-based catalysts can tolerate up to about 200 ppmw sulfur and 200 ppmw water, although these are less active than most chlorided-alumina catalysts. Metal oxide-based catalytic materials are intermediate in activity and can tolerate contaminants of sulfur and water at operating levels of less than 20 ppmw. These catalysts are typically zirconia-based because of their ability to generate super acids through sulfation. Some commercially available catalysts have water tolerances of up to at least about 30 ppmw. Unfortunately, while improvements to catalytic materials and catalysts that are water tolerant have been made, no commercially available catalytic materials or catalysts operate effectively at conditions of greater than 200 ppmw water in the wet hexanes feed stream.

The hydrothermal stability of zirconia under aqueous phase reforming conditions makes zirconia an attractive material for processing other feed stocks having a high water content. While zirconia is, in and of itself, an amphoteric material, the addition of tungsten or molybdenum has been shown to generate considerable Brönsted acidity. This acidity, though transient in the absence of gas-phase hydrogen, is not generated by the adsorption of strong acids, such as the case of sulfated zirconia and chlorided alumina. This makes materials such as tungsten-zirconia likely to perform acid catalyzed conversions in the presence of water. The hydrothermal stability of tungsten-zirconia is alleged to be true, although this is more of an assertion than a proven fact. Tungsten-zirconia catalysts have been used for hydration of propylene, aqueous hydrolysis of esters, aqueous esterification, and the hydration of ethylene, though the yields are low.

In the area of biofuels, the hydrogenation of glucose to sorbitol followed by hydrotreating of sorbitol to n-hexane often can result in an n-hexane stream containing up to about 30 weight percent water. Upgrading this n-hexane stream without the need to eliminate water would be advantageous for process heat integration and simplicity.

SUMMARY OF THE INVENTION

The current embodiment teaches a method to isomerize wet hexanes. The method begins by introducing one or more wet hexanes into a reactor under isomerization conditions to isomerize the wet hexanes. The wet hexanes comprise water and hexanes. The reactor contains a catalyst comprising tungsten, zirconium, and a Group VIII metal. In this embodiment the wet hexanes comprise from about 0.1 wt % to under 30 wt % water.

DETAILED DESCRIPTION

The following detailed description of various embodiments of the invention illustrates specific embodiments in which the invention can be practiced. The embodiments are intended to describe aspects of the invention in sufficient detail to enable those skilled in the art to practice the invention. Other embodiments can be utilized and changes can be made without departing from the scope of the present invention. The following detailed description is, therefore, not to be taken in a limiting sense. The scope of the present invention is defined only by the appended claims, along with the full scope of equivalents to which such claims are entitled.

Catalysts useful in the process of the presently pending invention are catalysts which comprise tungsten, zirconium, and a Group VIII metal ("Me"). Generally, the tungsten present in the final calcined catalyst comprises from 8 to about 30 weight percent, preferably 15 to about 30 weight percent, of the mass of the final, calcined catalyst composition and is in the form of metal (Me) tungstates ($Me^{+a}(WO_4)^{-2}_{a/2}$), wherein the metal (Me) is selected from the group consisting of nickel, zirconium, and mixtures thereof.

Zirconium present in catalysts useful in this invention is primarily in the form a zirconium oxide ($ZrO_2$) and is present within a range of about 55 to about 90 weight percent, preferably 55 to about 85 weight percent, based on the total mass of the calcined catalyst composition. Additionally, zirconium tungstates also can be present in minor quantities, and, if present, these zirconium tungstates are not considered part of the zirconium oxide that is present in the catalyst.

The Group VIII metal useful for catalysts of the present invention is selected from the group consisting of nickel, palladium, platinum, and mixtures thereof. Preferably, the Group VIII metal is present in a range of about 0.05 to about 6 weight percent. However, the amount of Group VIII metal present in the final calcined catalyst composition varies with the Group VIII metal used. For example, if the Group VIII metal is nickel, nickel usually is present within a range of about 2 to 5 weight percent, based on the mass of the total, final calcined catalyst composition. If the Group VIII metal is palladium, palladium also is present in a range of about 0.1 to 1 weight percent, based on the mass of the total, final calcined catalyst composition. If the Group VIII metal is platinum, generally, platinum is present in the final calcined catalyst composition within a range of about 0.1 to about 1 weight percent, based on the mass of the total, final calcined catalyst composition.

Catalysts useful in the present invention can be prepared by combining a known quantity of ammonium meta-tungstate and zirconium hydroxides. The composition is prepared by incipient wetness techniques and then calcined for a first time. Any calcination conditions can be used for calcination, but, for ease of use, calcination occurs under air at temperatures within the range of about 1110° F. to 1650° F. Upon this first calcination, while not wishing to be bound by theory, it is believed that the tungsten and zirconium react to produce a zirconium tungstate. After the first calcination, the Group VIII metal, such as nickel or platinum can be added and the composition again is calcined. At the conclusion of the second calcination, it is believed that the catalyst comprises zirconium oxides ($ZrO_2$), tungsten oxides ($WO_3$), zirconium tungstates ($Zr/WO_4$) and Group VIII metal tungstates ($M/WO_4$). Thus, if the Group VIII metal is nickel, nickel tungstates ($Ni/WO_4$) can be formed. If any excess nickel is present and has not reacted with the tungstate, nickel oxide (NiO) also can be present.

If platinum is selected and added as the Group VIII metal, the resultant catalyst has a similar composition to a catalyst having a similar composition comprising nickel. The catalyst composition comprises zirconium oxides, tungsten oxides, zirconium tungstates and platinum. However, while not wishing to be bound by theory, it is believed that the platinum does not react with tungstate to form a platinum tungstate.

Palladium also can work as the Group VIII metal. The amount of palladium present in the final, calcined catalyst composition can be within the range of about 0.1 to about 1 weight percent palladium, calculated either as palladium metal or any other form of palladium.

Often, zirconium precursors which can be used to prepare the catalyst compositions further comprise hafnium as an impurity in the zirconium component. Therefore, catalysts useful in the present invention optionally can comprise hafnium.

Catalysts of the present invention generally have a surface area of less than about 100 $m^2/g$. Preferably, the surface area of catalysts useful in the present invention is less than or equal to about 50 $m^2/g$. While not wishing to be bound by theory, it is believed that catalysts having a high surface area are more amorphous and therefore have less of a crystal structure. Further, while not wishing to be bound by theory, it is believed that a lower surface area catalyst can be more crystalline and therefore, can be more active. It is further believed that the presence of hafnium helps inhibit or prevent crystallinity.

Prior to the isomerization reaction, the catalyst must be reduced. Any reduction process known in the art can be employed, but reduction in the presence of hydrogen is preferred, due to availability and ease of use. Preferably, the catalyst can be added to the reactor and can be reduced on-stream in the reactor. Generally, the catalyst can be reduced at a pressure of about 200 psig and a temperature of about 700° F. Hydrogen can be fed at a rate of about 120 sccm (standard cubic centimeters per minute) and the catalyst reduction times of about 1 hour usually can be sufficient. Upon reduction of the catalyst, the reactor contents can be cooled to about 550° F. and the water-hydrocarbon mixture can be added for isomerization.

Isomerization process conditions useful in the present invention can be any conditions known to be useful to isomerize hexanes. As used in this invention, "hexanes" means any saturated, aliphatic hydrocarbon that comprises six carbon atoms. Wet hexanes are defined as hexanes that comprise of water and hexanes. In one embodiment the water content of the wet hexanes is less than 50 wt %, however it is possible that the water content is less than 30 wt %, 25 wt %, 20 wt %, 15 wt %, or even 10 wt %. In another embodiment the wt % of the water is from 0.1 wt % to 30 wt %, 0.1 wt % to less than 30 wt %, 1 wt % to 30 wt %, 1 wt % to 25 wt %, 1 wt % to 20 wt % or even 5 wt % to 20 wt %.

Any apparatus useful for isomerization also can be used. Any combination of temperature and pressure can be used in order to maintain water in the gas phase, i.e., steam. In accordance with this invention, it is essential that a substantial portion of the water present in the wet hexanes be present as steam, and preferably, at least about 95 weight percent of the water present in the wet hexanes be present as steam, and not as liquid water, during the isomerization reaction. Preferably, pressure in the isomerization reactor is within a range of about 50 to about 600 psig, preferably within a range of about 50 to about 300 psig, and most preferably, for optimal ease of use and reactivity, from 100 to 300 psig. The hydrogen to hydrocarbon molar ratio preferably is about 1:1 to about 20:1, and preferably about 3:1 to about 6:1. The liquid weight hourly space velocity (LWHSV) can be within a range of about 0.5 to about 20 $hr^{-1}$ and preferably within a range of about 1 to about 5 $hr^{-1}$. Generally, the reactor temperature can be within a range of about 300° F. to about 700° F., preferably within a range of about 400° F. to about 600° F., and most preferably, for ease of use and optimal reactivity, from 500° F. to 600° F.

Products of the isomerization of hexanes include, but are not limited to, 2,3-dimethylbutane and 2,2-dimethylbutane. Preferably, due to further commercial applications, a higher 2,2-dimethylbutane content is preferred.

EXAMPLES

Example 1

Catalyst Preparation

Catalyst A

Catalyst A was a commercially available platinum/zeolite catalyst used for isomerization of dry hexane streams, and was obtained from Zeolyst International as Z-700A and was used as provided. Catalyst A contained less than 1 wt % platinum, based on total catalyst weight. The balance was an aluminum oxide/zeolite carrier material. The catalyst was reduced on-stream at 700° F. and 200 psig for 1 hour in a 120 sccm hydrogen stream.

Catalyst B

Catalyst B was prepared by precipitation of amorphous $Zr(OH)_4$. A sufficient quantity of concentrated aqueous ammonium hydroxide was added drop-wise to a 0.25 molar aqueous solution of zirconyl chloride under vigorous stirring to obtain a final pH of 10.5-11. The zirconyl chloride contained a hafnium impurity. The resulting slurry was aged for 1 hour under vigorous stirring before being filtered and washed with approximately 3 times its volume of distilled water. The filter cake was dried in a vacuum oven for 2 days at 250° F. at approximately −7 psig. Once dry, the $Zr(OH)_4$ was washed a second time in approximately 3 times its volume of distilled water to remove all or a substantial portion of any residual chloride ions from the solid. The $Zr(OH)_4$ was dried overnight in a vacuum oven at 250° F. at approximately −7 psig. Tungsten was deposited on the zirconium hydroxide via incipient wetness impregnation using an aqueous solution of ammonium metatungstate (($NH_4)_6H_2W_{12}O_{40} \cdot xH_2O$) and was added drop-wise to the $Zr(OH)_4$ taken directly from the vacuum oven. The concentration of the ammonium metatungstate solution was adjusted to produce a final material containing 19.7 wt % W. The wetted support was dried overnight in a vacuum oven at 250° F. at approximately −7 psig. This dried material was calcined in air for three hours at 1380° F. The calcined support material was sized to 35-100 mesh prior to the addition of the hydrogenation metal. Platinum was subsequently added by incipient wetness impregnation to the calcined tungsten-zirconia that had been dried overnight in a vacuum oven (250° F., ~−7 psig) using aqueous solutions of chloroplatinic acid at a concentration sufficient to produce 0.5 wt % (based on the final composition) Pt material. The catalyst was again dried overnight in a vacuum oven (250° F., ~−7 psig) before being calcined at 930° F. for 3 hours in air. The calcined material was again sized to between 35 and 100 mesh.

Catalyst C

Catalyst C was prepared in the same manner as catalyst B except the concentration of the ammonium metatungstate solution was adjusted to result in a final calcined catalyst having a tungsten loading of 26.8 wt % and the zirconyl chloride did not contain a hafnium impurity. The chloroplatinic acid solution was also replaced with an aqueous solution of nickel (II) nitrate of sufficient concentration to result in a final calcined material containing 2.9 wt % nickel.

Catalyst D

Catalyst D was prepared in the same manner as catalyst C except the concentration of the ammonium metatungstate solution was adjusted to result in a final calcined catalysts with a tungsten loading of 26.0 wt %. The nickel (II) nitrate solution had a concentration sufficient to result in a final calcined material containing 5.0 wt % nickel.

Catalyst E

Catalyst E was prepared in the same manner as catalyst C except the concentration of the ammonium metatungstate solution was adjusted to result in a final calcined catalysts with a tungsten loading of 27.1 wt %. The nickel (II) nitrate solution had a concentration sufficient to result in a final calcined material containing 2.9 wt % nickel.

A summary of Catalysts B, C, D, and E is presented in Table 1.

TABLE 1

Catalyst Characteristics

| Catalyst | Metal Content (wt %) | Tungsten Content (wt %) | Hafnium Content (wt %) | Zirconia Content (wt %) | Surface Area ($m^2/g$) |
|---|---|---|---|---|---|
| B | 0.5 Pt | 19.7 | 1.8 | 68.6 | 58.2 |
| C | 2.9 Ni | 26.8 | — | 59.7 | 49.0 |
| D | 5.0 Ni | 26.0 | — | 60.1 | 50.2 |
| E | 2.8 Ni | 27.1 | — | 59.7 | 47.8 |

Example 2

Isomerization of Wet Hexanes

Catalyst A

Catalyst A was cooled to 550° F. before introducing a water and n-hexane feed stream which contained 30 wt % water. Hydrogen was supplied to the reactor at a volume sufficient to produce a hydrogen to n-hexane molar ratio of 5. The flow rate was adjusted to result in a liquid weight hourly space velocity (LWHSV) of 2 $hr^{-1}$. Liquid samples were collected in a wet ice knock out flask every 30 minutes after the appearance of liquid products. Results are shown below in Table 2.

TABLE 2

Results of contacting wet hexane with Catalyst A

| Collection | Time on Stream (min) | 2,2-Dimethylbutane Yield (%) | 2,3-Dimethylbutane Yield (%) | Dimethylbutanes Yield (%) | n-Hexane Conversion (%) |
|---|---|---|---|---|---|
| 1 | 0 | 0.042 | 0.195 | 0.237 | 0.97 |
| 2 | 30 | 0.023 | 0.149 | 0.172 | 0.60 |
| 3 | 60 | 0.026 | 0.133 | 0.159 | 0.50 |
| 4 | 90 | 0.020 | 0.137 | 0.157 | 0.47 |
| 5 | 120 | 0.020 | 0.136 | 0.156 | 0.47 |
| 6 | 150 | 0.021 | 0.135 | 0.156 | 0.48 |
| 7 | 180 | 0.020 | 0.139 | 0.159 | 0.49 |
| 8 | 210 | 0.021 | 0.135 | 0.156 | 0.46 |
| 9 | 240 | 0.019 | 0.136 | 0.155 | 0.47 |
| 10 | 270 | 0.021 | 0.136 | 0.157 | 0.48 |

The data in Table 2 show yields of wet n-hexane to dimethylbutanes and conversions of wet n-hexane with a commercially available catalyst.

Catalyst B

The evaluation of Catalyst B for the isomerization of wet n-hexane was carried out in the same manner as Catalyst A. Results are presented in Table 3, below.

TABLE 3

Results of contacting wet hexanes with Catalyst B

| Collection | Time on Stream (min) | 2,2-Dimethylbutane Yield (%) | 2,3-Dimethylbutane Yield (%) | Dimethylbutanes Yield (%) | n-Hexane Conversion (%) |
|---|---|---|---|---|---|
| 1 | 0 | 9.377 | 7.065 | 16.442 | 72.0 |
| 2 | 30 | 8.383 | 6.772 | 15.155 | 69.8 |
| 3 | 60 | 7.660 | 6.494 | 14.154 | 68.0 |
| 4 | 90 | 7.481 | 6.464 | 13.945 | 68.0 |
| 5 | 120 | 7.026 | 6.385 | 13.411 | 67.7 |
| 6 | 150 | 7.609 | 6.577 | 14.186 | 68.6 |

TABLE 3-continued

Results of contacting wet hexanes with Catalyst B

| Collection | Time on Stream (min) | 2,2-Dimethylbutane Yield (%) | 2,3-Dimethylbutane Yield (%) | Dimethylbutanes Yield (%) | n-Hexane Conversion (%) |
|---|---|---|---|---|---|
| 7 | 180 | 7.016 | 6.248 | 13.264 | 66.5 |
| 8 | 210 | 6.627 | 6.123 | 12.750 | 65.6 |
| 9 | 240 | 5.615 | 5.301 | 10.916 | 60.3 |
| 10 | 270 | 6.252 | 6.072 | 12.324 | 65.2 |

The data in Table 3 shows that under identical reaction conditions, Catalyst B has a higher conversion of n-hexane to dimethylbutanes, as evidenced by higher dimethylbutanes yields, than Catalyst A.

Catalyst C

Catalyst C was evaluated under the same conditions as Catalyst B, above. Reactivity results are presented in Table 4, below.

TABLE 4

Results of contacting wet n-hexane with Catalyst C

| Collection | Time on Stream (min) | 2,2-Dimethylbutane Yield (%) | 2,3-Dimethylbutane Yield (%) | Dimethylbutanes Yield (%) | n-Hexane Conversion (%) |
|---|---|---|---|---|---|
| 1 | 0 | 0.293 | 1.475 | 1.768 | 13.1 |
| 2 | 30 | 0.160 | 0.895 | 1.055 | 8.0 |
| 3 | 60 | 0.325 | 1.514 | 1.839 | 13.1 |
| 4 | 90 | 0.260 | 1.330 | 1.590 | 11.9 |
| 5 | 120 | 0.190 | 0.969 | 1.159 | 8.7 |
| 6 | 150 | 0.177 | 0.865 | 1.042 | 7.6 |
| 7 | 180 | 0.176 | 0.894 | 1.070 | 8.0 |
| 8 | 210 | 0.198 | 0.953 | 1.151 | 8.4 |
| 9 | 240 | 0.157 | 0.816 | 0.973 | 7.4 |
| 10 | 270 | 0.149 | 0.745 | 0.894 | 6.6 |

The data in Table 4 show that nickel-based catalysts, like Catalyst C, can isomerize wet n-hexane to dimethylbutanes.

Catalyst D

Catalyst D was evaluated under the same conditions as Catalyst B, above. Reactivity results are presented in Table 5, below.

TABLE 5

Results of contacting wet hexane with Catalyst D

| Collection | Time on Stream (min) | 2,2-Dimethylbutane Yield (%) | 2,3-Dimethylbutane Yield (%) | Dimethylbutanes Yield (%) | n-Hexane Conversion (%) |
|---|---|---|---|---|---|
| 1 | 0 | 1.535 | 2.452 | 3.987 | 36.2 |
| 2 | 30 | 0.615 | 1.385 | 2.000 | 22.4 |
| 3 | 60 | 0.625 | 1.315 | 1.940 | 22.0 |
| 4 | 90 | 0.476 | 1.075 | 1.551 | 19.3 |
| 5 | 120 | 0.411 | 0.907 | 1.318 | 17.7 |
| 6 | 150 | 0.377 | 0.830 | 1.207 | 16.7 |
| 7 | 180 | 0.268 | 0.654 | 0.922 | 14.0 |
| 8 | 210 | 0.255 | 0.605 | 0.860 | 13.0 |
| 9 | 240 | 0.241 | 0.574 | 0.815 | 12.6 |
| 10 | 270 | 0.260 | 0.626 | 0.886 | 13.3 |

The data in Table 5 shows that nickel-based catalysts with higher nickel loadings, like Catalyst D, can isomerize wet n-hexane to dimethylbutanes.

Catalyst E

Catalyst E was evaluated in the same manner as Catalyst B, above. Reactivity results are presented in Table 6, below.

TABLE 6

Results of contacting wet n-hexane with Catalyst E

| Collection | Time on Stream (min) | 2,2-Dimethylbutane Yield (%) | 2,3-Dimethylbutane Yield (%) | Dimethylbutanes Yield (%) | n-Hexane Conversion (%) |
|---|---|---|---|---|---|
| 1 | 0 | 1.046 | 3.692 | 4.738 | 33.1 |
| 2 | 30 | 0.705 | 2.558 | 3.263 | 24.2 |
| 3 | 60 | 0.836 | 2.882 | 3.718 | 27.4 |
| 4 | 90 | 0.745 | 2.528 | 3.273 | 25.0 |
| 5 | 120 | 0.683 | 2.316 | 2.999 | 23.1 |
| 6 | 150 | 0.685 | 2.283 | 2.968 | 22.8 |
| 7 | 180 | 0.646 | 2.198 | 2.844 | 22.6 |
| 8 | 210 | 0.608 | 2.086 | 2.694 | 21.4 |
| 9 | 240 | 0.493 | 1.768 | 2.261 | 19.0 |
| 10 | 270 | 0.474 | 1.715 | 2.189 | 18.3 |

The data in Table 6 shows that nickel-based catalysts with lower nickel loadings, like Catalyst E, can isomerize wet n-hexane to dimethylbutanes.

Example 3

Isomerization of Wet Hexanes

Catalyst B was evaluated under the conditions of Catalyst A in Example 2, above, except that the reaction temperature reduced to 400° F.

TABLE 7

Results of contacting wet hexane with Catalyst B

| Collection | Time on Stream (min) | 2,2-Dimethylbutane Yield (%) | 2,3-Dimethylbutane Yield (%) | Dimethylbutane Yield (%) | n-Hexane Conversion (%) |
|---|---|---|---|---|---|
| 1 | 0 | 0.083 | 0.488 | 0.571 | 8.2 |
| 2 | 30 | 0.048 | 0.308 | 0.356 | 4.9 |
| 3 | 60 | 0.023 | 0.178 | 0.201 | 2.3 |
| 4 | 90 | 0.010 | 0.087 | 0.097 | 0.6 |
| 5 | 120 | 0.010 | 0.071 | 0.081 | 0.2 |
| 6 | 150 | 0.011 | 0.099 | 0.110 | 0.1 |
| 7 | 180 | 0.013 | 0.103 | 0.116 | 0.2 |
| 8 | 210 | 0.011 | 0.100 | 0.111 | 0.3 |
| 9 | 240 | 0.012 | 0.096 | 0.108 | 0.2 |
| 10 | 270 | 0.012 | 0.099 | 0.111 | 0.2 |

The data in Table 7, Example 3, shows that at temperatures lower than in Example 2, Catalyst B can isomerize n-hexane and produce dimethylbutanes.

Example 4

Isomerization of Dry Hexanes

Catalysts F, G, H, I, J, K, L, M, N, O, P, Q, R, S, T and U were prepared in a manner identical to Catalyst C except for a change in temperature for the first calcination step and the elimination of the first sieving of each catalyst prior to nickel addition. Nickel (II) nitrate and ammonium metatungstate solution concentrations were adjusted to result in the metal loadings shown in Table 8.

These catalysts were evaluated for the dry isomerization of a 5 wt % cyclohexane in n-hexane feed. Each catalyst was pretreated in the same manner as Catalyst A. Following reduction, each catalyst was cooled to 550° F. At 550° F., the cyclohexane/n-hexane mixture was fed to the reactor and the hydrogen flow rate was adjusted to result in a hydrogen to hydrocarbon mole ratio of about 0.7. The LWHSV was about 17 $hr^{-1}$. The results are shown in table 8, below.

TABLE 8

Composition and initial n-hexane isomerization activity for Catalysts F through U.

| Catalyst | Tungsten Loading (wt %) | Nickel Loading (wt %) | Hafnium Impurity (wt %) | Calcination Temperature (° F.) | Surface Area (m2/g) | Initial n-Hexane Conversion (%) |
|---|---|---|---|---|---|---|
| F | 18.2 | 3.32 | — | 1110 | 102 | 23.8 |
| G | 16.4 | 2.54 | — | 1290 | 54.7 | 28.7 |
| H | 16.2 | 2.78 | — | 1470 | 48.9 | 21.6 |
| I | 17.0 | 2.74 | 1.41 | 930 | 125 | 2.2 |
| J | 16.4 | 3.18 | 1.38 | 1110 | 82.5 | 14.8 |
| K | 16.2 | 3.04 | 1.41 | 1290 | 66.6 | 20.8 |
| L | 16.9 | 2.33 | — | 1650 | 32.4 | 25.0 |
| M | 16.7 | 2.26 | 1.41 | 1470 | 41.6 | 22.3 |
| N | 16.2 | 2.78 | — | 1200 | 50.2 | 26.0 |
| O | 8.7 | 3.4 | 1.7 | 1110 | 93 | 1.87 |
| P | 16.1 | 3.1 | 1.5 | 1110 | 123 | 5.90 |
| Q | 20.2 | 2.1 | 1.1 | 1110 | 146 | 4.55 |
| R | 18.5 | 3.3 | 1.4 | 1110 | 125 | 4.80 |
| S | 35.4 | 2.2 | 1.0 | 1110 | 113 | 2.94 |
| T | 43.3 | 3.1 | 1.1 | 1110 | 97 | 2.77 |
| U | 12.6 | 3.0 | 0.7 | 1110 | 125 | 4.95 |

The data in Table 8 shows that isomerization activity generally increases with decreasing catalyst surface area. This data shows that low surface area catalysts generally are more crystalline and therefore more active for the conversion of hydrocarbons.

Numerical Ranges

The present description uses numerical ranges to quantify certain parameters relating to the invention. It should be understood that when numerical ranges are provided, such ranges are to be construed as providing literal support for claim limitations that only recite the lower value of the range as well as claims limitation that only recite the upper value of the range. For example, a disclosed numerical range of 10 to 100 provides literal support for a claim reciting "greater than 10" (with no upper bounds) and a claim reciting "less than 100" (with no lower bounds).

Definitions

As used herein, the terms "comprising," "comprises," and "comprise" are open-ended transition terms used to transition from a subject recited before the term to one or more elements recited after the term, where the element or elements listed after the transition term are not necessarily the only elements that make up the subject.

As used herein, the terms "including," "includes," and "include" have the same open-ended meaning as "comprising," "comprises," and "comprise."

As used herein, the terms "having," "has," and "have" have the same open-ended meaning as "comprising," "comprises," and "comprise."

As used herein, the terms "containing," "contains," and "contain" have the same open-ended meaning as "comprising," "comprises," and "comprise."

As used herein, the terms "a," "an," "the," and "said" mean one or more.

As used herein, the term "and/or," when used in a list of two or more items, means that any one of the listed items can be employed by itself or any combination of two or more of the listed items can be employed. For example, if a composition is described as containing components A, B, and/or C, the composition can contain A alone; B alone; C alone; A and B in combination; A and C in combination; B and C in combination; or A, B, and C in combination.

Claims Not Limited to the Disclosed Embodiments

The preferred forms of the invention described above are to be used as illustration only, and should not be used in a limiting sense to interpret the scope of the present invention. Obvious modifications to the exemplary embodiments, set forth above, could be readily made by those skilled in the art without departing from the spirit of the present invention.

The inventors hereby state their intent to rely on the Doctrine of Equivalents to determine and assess the reasonably fair scope of the present invention as pertains to any apparatus not materially departing from but outside the literal scope of the invention as set forth in the following claims.

That which is claimed:

1. A method to isomerize wet hexanes comprising:
 a) introducing one or more wet hexanes into a reactor under isomerization conditions to isomerize wet hexanes,
 wherein said wet hexanes comprise water and hexanes;
 wherein said reactor contains a catalyst comprising tungsten, zirconium and a Group VIII metal;
 wherein said wet hexanes comprise from about 1 wt % to under 30 wt % water and the surface area of said catalyst is less than about 100m$^2$/g.

2. The method of claim 1, wherein said isomerization conditions comprise a pressure and temperature sufficient to maintain said water in a gas phase.

3. The method of claim 1, wherein said isomerization conditions comprise a temperature within a range of about 400° F. to about 700° F. and a pressure within a range of about 100psig to about 300 psig.

4. The method of claim 1, wherein hydrogen is added to said reactor prior to introduction of said wet hexanes.

5. The method of claim 4, wherein the ratio of said hydrogen to said hexanes is within a molar ratio of about 1:1 to about 20:1.

6. The method of claim 1, wherein said reactor has a liquid weight hourly space velocity of about 0.5 hour$^{-1}$ to about 20 hour$^{-1}$.

7. The method of claim 1, wherein said catalyst composition comprises;

a) metal tungstates;
b) zirconium oxides; and
c) a metal selected from the group consisting of nickel, platinum, palladium, and mixtures thereof.

8. The method of claim 1, wherein said catalyst further comprises metal tungstates having a composition of $(Me^{+a}(WO_4)^{-2}{}_{a/2})$, and wherein the metal (Me) is selected from the group consisting of nickel, zirconium, and mixtures thereof.

9. A method to isomerize wet hexanes comprising:
a) introducing one or more wet hexanes into a reactor under isomerization conditions to isomerize wet hexanes,
wherein said wet hexanes comprise water, in the amount of at least 95% steam, and hexanes;
wherein said reactor contains a catalyst comprising tungsten, zirconium and a Group VIII metal;
wherein said wet hexanes comprise from about $1_{13}$ wt % to under 30 wt % water and the surface area of said catalyst is less than about 100m$^2$/g; and
wherein the isomerization conditions comprise a temperature within a range of about 400° F. to about 700° F. and a pressure within a range of about 100_psig to about 300 psig.

* * * * *